United States Patent [19]

Rust

[11] Patent Number: 4,692,415
[45] Date of Patent: Sep. 8, 1987

[54] PROCESS FOR THE DETERMINATION OF CYANAMIDE IN PLANTS AND PLANT PARTS

[75] Inventor: Ulrich Rust, Trostberg, Fed. Rep. of Germany

[73] Assignee: SKW Trostberg Aktiengesellschaft, Trostberg, Fed. Rep. of Germany

[21] Appl. No.: 896,950

[22] Filed: Aug. 14, 1986

[30] Foreign Application Priority Data

Aug. 22, 1985 [DE] Fed. Rep. of Germany ....... 3530013
Jul. 25, 1986 [DE] Fed. Rep. of Germany ....... 3625205

[51] Int. Cl.$^4$ .................... G01N 33/00; G01N 33/02
[52] U.S. Cl. ...................................... 436/20; 436/109
[58] Field of Search ................................ 436/20, 109

[56] References Cited
PUBLICATIONS

Buyske et al., "Spectrophotometric Determination of Cyanamide", Analyt. Chem., 32, 1798–1800, 1960.
Nieman et al., "Reaction Rate Method for Determining Trace Concentations of Cyanamide", Analyt. Chem., 48, 899–902, 1976.

*Primary Examiner*—Michael S. Marcus
*Assistant Examiner*—Floyd E. Bennett, Jr.
*Attorney, Agent, or Firm*—Felfe & Lynch

[57] ABSTRACT

The present invention provides a process for the determination of cyanamide in plants or plant parts, wherein
(a) the cyanamide is extracted from the plants,
(b) it is subsequently reacted in aqueous alkaline medium with 1,2-naphthoquinone-4-sulphonate to give 4-cyanimido-1,2-naphthoquinone,
(c) this reaction product is separated by high performance liquid chromatography on a reverse phase and
(d) it is determined spectrophotometrically at a wavelength of 485 nm or 272 nm.

21 Claims, 4 Drawing Figures

PROCESS FOR THE DETERMINATION OF CYANAMIDE IN PLANTS AND PLANT PARTS

The present invention is concerned with a process for the determination of cyanamide in plants or plant parts and especially in fruits.

According to Federal Republic of Germany Patent Specification No. 31 50 404, cyanamide can be used as an agent for breaking bud dormancy, especially in the case of grapes and other fruits. For reasons of environmental protection, it is desirable to exactly determine the residual content of cyanamide in these plants. Hitherto, however, no practical analysis method has been known in order to detect cyanamide in trace amounts with sufficient accuracy.

The previously used detection methods depend upon the strong electron withdrawing action of the cyano group and the acidity resulting therefrom of the NH protons of the cyanamide, which can easily be substituted in alkaline medium. The formation of silver cyanamide was especially utilised in a series of analysis processes (cf. R. Perotte, Gazz. Chim. Ital., 35, 228/1905) for the content determination. However, contents below 0.1% cyanamide cannot be determined with these methods. For a series of colorimetric processes, chlorocyanamide forms the reaction intermediate stage for the detection of cyanamide but exact determinations in trace amounts are still not possible with these methods.

In an alkaline medium, cyanamide can be incorporated as ligand into cyanoferrates, the coloured complexes resulting therefrom being utilized for the determination of cyanamide in trace amounts (cf. D.A. Buyske and V. Downing, Anal. Chem., 32, 1798/1960). A disadvantage of these methods is their non-specificity since a number of other nucleophilic compounds also give this colour reaction and the necessary separation of these disturbing substances before the colour reaction is rather problematical.

The previously described paper and thin layer chromatographic methods of analysis, in which, as colour reagent there is used, for example, 1,2-naphthoquinone-4-sulphonate, are also not sensitive enough.

Therefore, it is an object of the present invention to provide a process for the determination of cyanamide in plants or plant parts which does not display these disadvantages of the prior art but rather, in a simple manner, makes possible a problem-free measurement method of high sensitivity and sufficient accuracy and which is also especially useful for detecting trace amounts of cyanamide.

Thus, according to the present invention, there is provided a process for the determination of cyanamide in plants or plant parts, wherein
(a) the cyanamide is extracted from the plants,
(b) it is subsequently reacted in aqueous alkaline medium with 1,2-naphthoquinone-4-sulphonate to give 4-cyanimido-1,2-naphthoquinone,
(c) this reaction product is separated by high pressure liquid chromatography on a reverse phase and
(d) it is determined spectrophotometrically at a wavelength of 485 nm or 272 nm.

Surprisingly, we have found that, with the help of the process according to the present invention, cyanamide can be detected extremely specifically and sensitively also in the presence of disturbing substances, for example amino acids.

According to the present invention, the plants or plant parts, especially grapes, are comminuted with technically conventional devices and the cyanamide, which is then present in aqueous solution, is isolated from the fruits by extraction, this preferably taking place by liquid-liquid extraction. As solvents for the liquid-liquid extraction, there can be used all water-insoluble organic solvents which display a sufficient partition coefficient with regard to the cyanamide in comparison with water, esters, such as ethyl acetate, or ethers, such as diethyl ether, having thereby proved to be especially advantageous. The nature of the carrying out of the liquid-liquid extraction can take place in any desired way. In the simplest embodiment, the cyanamide is extracted in one of the usual extraction apparatus or is obtained by shaking out the aqueous phase several times with an appropriate solvent. In a preferred embodiment, the cyanamide-containing aqueous solution is separated from insoluble fruit residue and the cyanamide subsequently isolated by liquid-liquid extraction, preferably on a solid adsorbent. As extraction agents, there can also be used the above-mentioned water-insoluble organic solvents or mixtures thereof. The solid adsorbent used is preferably kieselguhr, especially diatomaceous earth, but, in principle, other adsorbents, for example silica gel and the like, can also be used.

After isolation of the cyanamide, possibly together with other plant component materials, the organic solvent is removed and subsequently the reaction of the 1,2-naphthoquinone-4-sulphonate is carried out with the cyanamide in aqueous alkaline solution. The pH value used can be from 8 to 12 and preferably from 9.5 to 10.5 in order to achieve a quickest possible reaction. The pH value adjustment can be carried out with conventional alkaline reagents, such as potassium or sodium hydroxide or sodium or potassium carbonate. The reaction temperature is also an important factor for the speed of the reaction. It should be from 10° to 150° C. and preferably from 80° to 120° C. in order that, on the one hand, the reaction takes place relatively quickly but, on the other hand, no decomposition of the cyanamide or of the reaction product between the cyanamide and the 1,2-naphthoquinone-4-sulphonate takes place. The amount of 1,2-naphthoquinone-4-sulphonate used, which is preferably used as the sodium salt, depends, essentially upon the cyanamide content of the sample. The 1,2-naphthoquinone-4-sulphonate must be available in an at least stoichiometric amount in order to make possible a quantitative reaction with the cyanamide. It is preferable to use a 10 to 100 fold excess, referred to the expected cyanamide content. The concentration of the solution of the 1,2-naphthoquinone-4-sulphonate can be varied in wide limits, a concentration of 500 to 1500 mg. per 1000 ml. of reaction solution being preferred.

In the case of the reaction of the cyanamide with the 1,2-naphthoquinone-4-sulphonate in an alkaline medium, there results the sodium or potassium salt of the 4-cyanamido-1,2-naphthoquinone as an orange-red coloured material. In addition, in the reaction, by-products are also formed which must be separated off in a subsequent high performance liquid chromatography (HPLC). For the working up for the HPLC, the aqueous reaction solution is, after cooling, preferably mixed with a tetraalkylammonium salt and subsequently the resultant tetraalkylammonium salt of the 4-cyanamido-1,2-naphthoquinone is extracted with a water-insoluble organic solvent.

The tetraalkylammonium salt improves the retention of the naphthoquinone derivative in the subsequent reverse phase HPLC and thus makes easier a separation from the by-products. There can thereby be used conventional tetraalkylammonium salts with the same or different alkyl groups, each of which contains 1 to about 12 carbon atoms, for example with methyl, ethyl, propyl, butyl and/or octyl groups, as well as the usual anions, for example fluoride, chloride, bromide, iodide, hydroxide, acetate or hydrogen sulphate and methyltrioctylammonium chloride have hereby proved to be especially useful.

As solvents for the extraction of the 4-cyanimido-1,2-naphthoquinone, it is especially preferred to use chlorinated hydrocarbons, such as dichloromethane, chloroform or carbon tetrachloride. However, other solvents can also be used, such as hydrocarbons, for example toluene.

After the extraction of the 4-cyanimido-1,2-naphthoquinone and possibly of the by-products, the solvent is completely removed, for example on a rotary evaporator, and the residue subsequently taken up with the elution agent intended for the high performance liquid chromatography. Before the application to the HPLC system, the liquid mixture is preferably freed from solid particles possibly present by means of a membrane filter.

In the subsequent high performance liquid chromatography on a reverse phase, preferably on a commercially available C-8 reverse phase, there then takes place the separation of the reaction products. The mobile phase used is preferably a mixture conventional for ion pair chromatography, especially the methyltrioctylammonium salt and methanol/water buffer (ratio 850:100:50 to 600:350:50). The buffer has, a pH value of 4.0 to 7.0 and consists, e. g., of disodium hydrogen phosphate and potassium dihydrogen phosphate or sodium citrate. The amount of methyltrioctylammonium salt, for example, chloride, is normally from 0.1 to 2.0 g. per 1000 ml. methanol/water buffer solution. The spectrophotometric determination of the 4-cyanimido-1,2-naphthoquinone derivative can take place at a wavelength of 485 nm or 272 nm. The cyanamide content can then be determined by evaluation of the peak height in comparison with a standard solution (0.01 mg. cyanamide).

With the help of the process according to the present invention, the cyanamide content can be detected relatively simply and problem free with a lower limit of determination of 0.01 to 0.05 ppm.

For further illustration, reference is made to FIGS. 1 to 4 of the accompanying drawings which show HPLC chromatograms which have been obtained with the process of the present invention.

Figure 1:
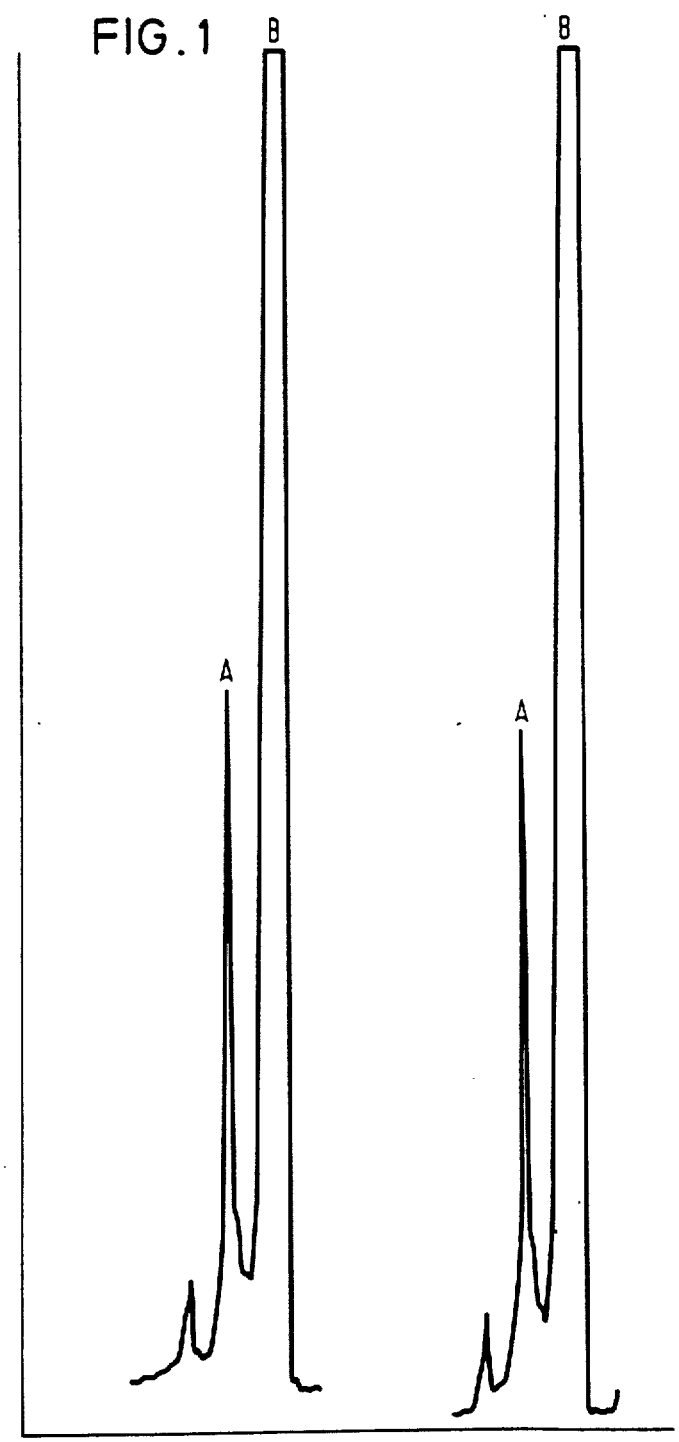
FIG. 1 shows a chromatogram which was obtained by double application of a standard solution with a content of 10 μg. cyanamide, peak A being the cyanamide peak and peak B the by-product or reagent peak.
Figure 2:
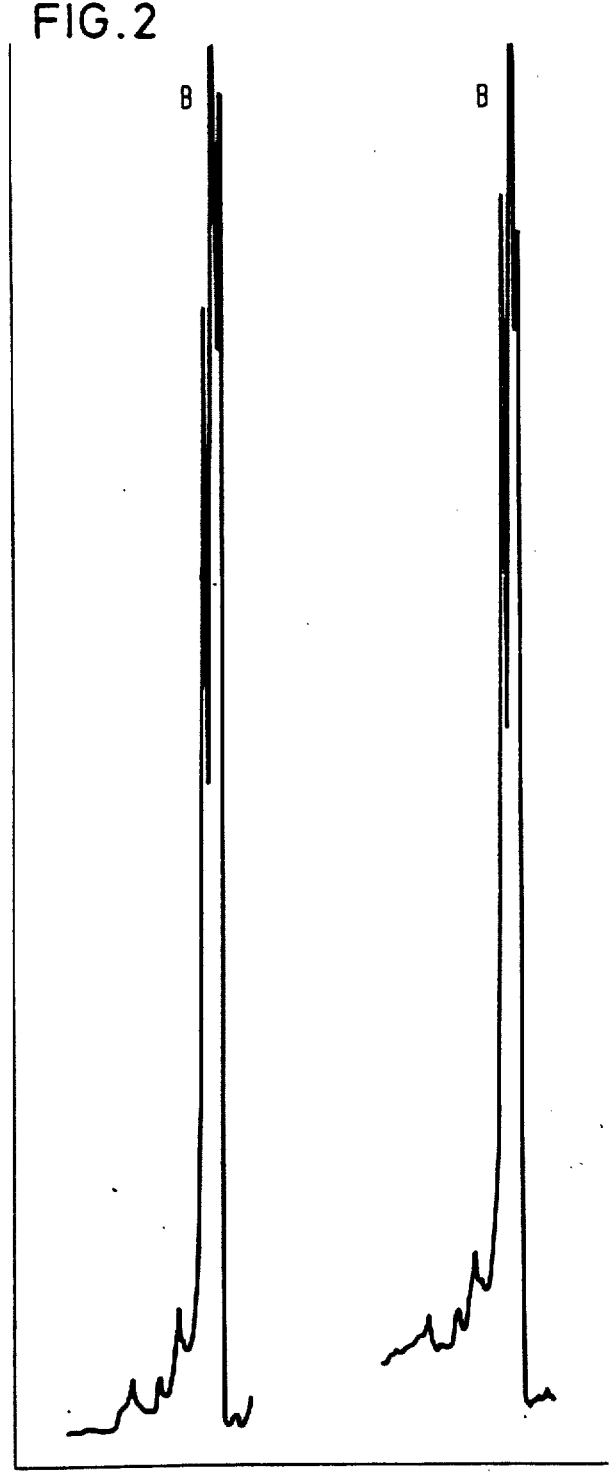
FIG. 2 shows a chromatogram which was obtained starting from untreated, ripe grapes, peaks B being disturbance peaks which orginate from plant component materials.
Figure 3:
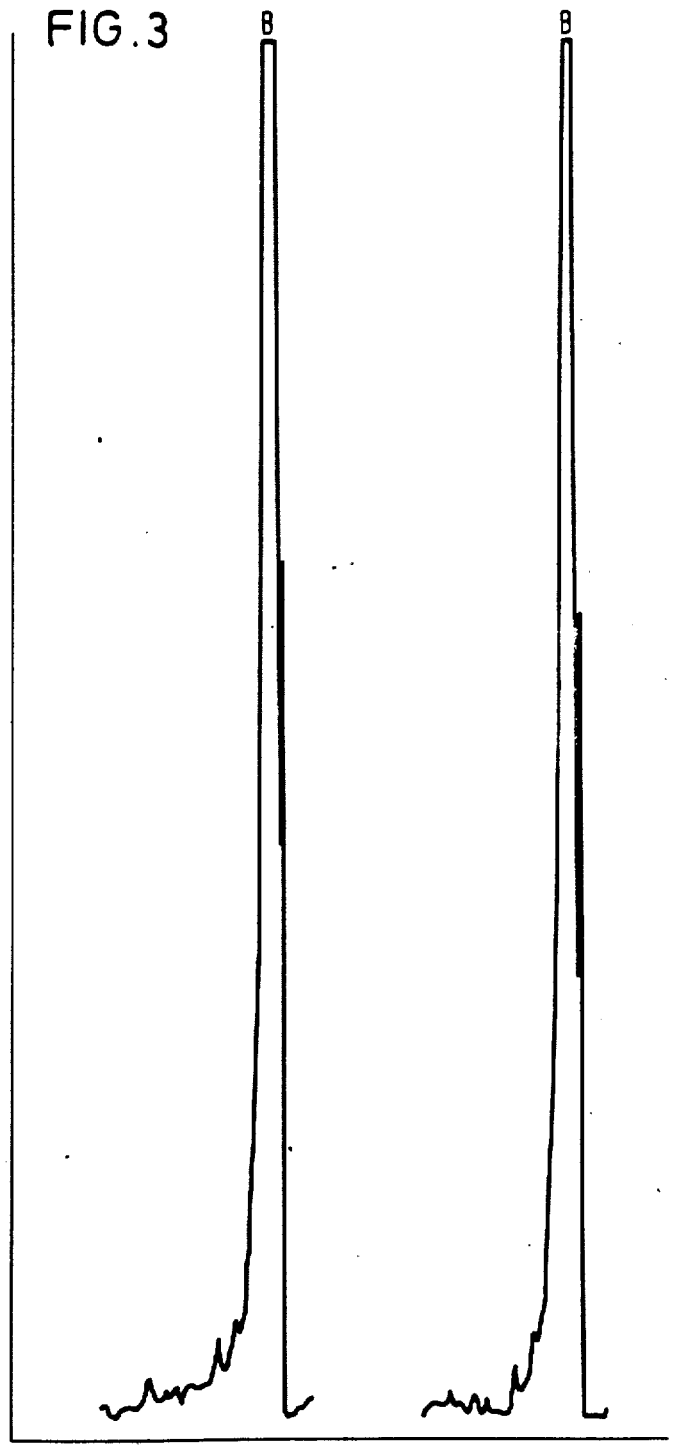
FIG. 3 shows a corresponding HPLC chromatogram which was obtained starting from ripe grapes which had been treated with cyanamide. It can be seen that practically no cyanamide is detected, only disturbance peaks B being recognised.
Figure 4:
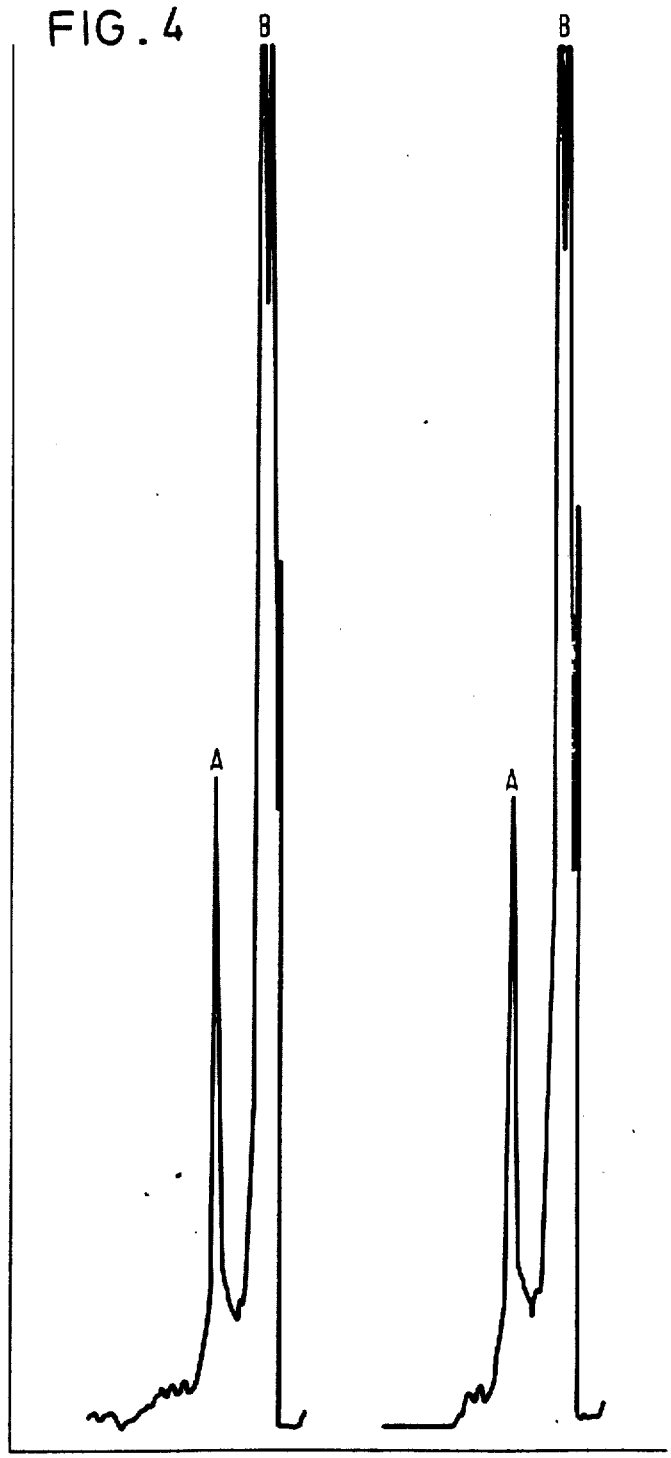
FIG. 4 shows chromatograms which, starting from untreated grapes, had been additionally mixed with 10 μg. cyanamide. Peak A again corresponds to the cyanamide peak and peaks B are disturbance peaks.

The following Example is given for the purpose of illustrating the present invention:

EXAMPLE

(A) Sample Preparation 50 g. of grapes are comminuted in a mixer and then rinsed with a little water in a 250 ml. Erlenmeyer flask and placed for 5 minutes in an ultrasonic bath. Thereafter, it is centrifuged and the supernatant decanted off. The precipitate is washed twice with 20 ml. amounts of water and centrifuged. The combined supernatants are adjusted by means of sodium hydroxide to a pH value of 5.8 to 6.2 and concentrated to about 20 ml. at a maximum bath temperature of 35° C. on a rotary evaporator. The sample solution is now taken up with 10 g. Extrelut (Merck Art. No. 11738) and quantitatively applied to a diatomaceous earth-containing finished column (trade name CT 2050 of the firm ICT) which had previously been loaded with 10 ml. water. Elution is commenced immediately with 400 ml. ethyl acetate. With the addition of 30 ml. water, the ester is stripped off on a rotary evaporator at a maximum temperature of 35° C. The remaining solution is used for the following reaction with 1,2-naphthoquinone-4-sulphonate.

(B) Reaction and Determination

The sample solution is mixed with 5 ml. naphthoquinone solution (concentration 1 g. 1,2-naphthoquinone-4-sulphonate per 100 ml. water) and with 10 ml. sodium carbonate solution (concentration 0.2 mole/liter) and heated for 5 minutes in an oil bath to a temperature of 100° C. Subsequently, the sample solution is cooled to ambient temperature with an ice bath and transferred quantitatively (after-rinsed with a few ml. of water) to a separating funnel. It is now shaken out four times with, in each case, 30 ml. dichloromethane, with the addition of, in each case, 1 ml. tetrabutylammonium hydrogen sulphate solution (concentration 0.1 mole/liter). The combined organic phases are evaporated to dryness at 35° C. on a rotary evaporator. The residue is taken up with 5 ml. methanol and, after filtration through a membrane filter, applied to the HPLC system.

As standard, 0.01 mg. cyanamide are analysed in the same way.

(C) Chromatographic Conditions

HPLC system: Kontron HPLC 600
UV/VIS detector: Kontron LC 720 (digital resolution 0.07 AUFS)
mobile phase:
  0.5 g. methyltrioctylammonium chloride are dissolved in 1000 ml. methanol/water phosphate buffer 750+200+50.
  Phosphate buffer: 610 ml. Solution I and 390 ml. Solution II are mixed.
  Solution I: 11.8 g. disodium hydrogen phosphate are dissolved with water to give 1000 ml.
  Solution II: 9.0 g. potassium dihydrogen phosphate are dissolved with water to give 1000 ml.
separation column: Zorbax C8, 4.6×250 mm. (Du Pont Instr.)
flowthrough rate: 0.8-1.2 ml./minute
measurement wavelength: 485 nm

(D) Evaluation

The evaluation takes place according to the following equation:

$$\text{ppm Cy} = (\text{HPr} \times \text{Add}) / (\text{Hv} \times \text{Ein})$$

ppm CY = cyanamide content in the sample (mg./kg.)
HPr = peak height of the signal from the sample
Add = cyanamide amount in the standard (μg.)
HV = peak height of the comparison signal
Ein = weighed amount of sample (g.)

I claim:

1. A process for the determination of cyanamide in plants or plant parts, comprising
    (a) extracting cyanamide from plants or plant parts,
    (b) reacting the cyanamide in aqueous alkaline medium with 1,2-naphthoquinone-4-sulphonate to give 4-cyanimido-1, 2-naphthoquinone,
    (c) separating the 4-cyanamido-1,2-naphthoquinone from the aqueous medium by high performance liquid chromatography on a reverse phase and
    (d) determining the 4-cyanimido-1, 2-naphthoquinone spectrophotometrically at a wavelength of 485 nm or 272 nm as a measure of the cyanamide extracted from the plants or plant parts.

2. The process of claim 1, wherein an aqueous plant or plant parts extract is produced and the cyanamide is extracted from the aqueous extract by liquid-liquid extraction.

3. The process of claim 2, wherein the liquid-liquid extraction of the cyanamide dissolved in the water is carried out with the help of a water-insoluble, organic solvent.

4. The process of claim 3, wherein the organic solvent is ethyl acetate or diethyl ether.

5. The process of claim 4 wherein the reaction of the cyanamide with the 1,2-naphthoquinone-4-sulphonate is carried out in the pH range of from 8 to 12.

6. The process of claim 5, wherein the reaction of the cyanamide with the 1,2-naphthoquinone-4-sulphonate is carried out in the pH range of from 9.5 to 10.5.

7. The process of claim 2 wherein the cyanamide is extracted from the aqueous extract by liquid-liquid extraction on a solid adsorbent.

8. The process of claim 7, wherein the solid adsorbent is kieselguhr.

9. The process of claim 8, wherein the kieselguhr is diatomaceous earth.

10. The process of claim 1 wherein the reaction of the cyanamide with the 1,2-naphthoquinone-4-sulphonate is carried out at a temperature of from 10° to 150° C.

11. The process of claim 10, wherein the reaction of the cyanamide with the 1,2-naphthoquinone-4-sulphonate is carried out at a temperature of from 80° to 120° C.

12. The process of claim 1 wherein the reaction product of cyanamide and 1,2-naphthoquinone-4-sulphonate is used in the high performance liquid chromatography as a tetraalkylammonium salt.

13. The process of claim 12, wherein, for the preparation of the tetraalkylammonium salt, tetrabutylammonium hydrogen sulphate or methyltrioctylammonium chloride is used.

14. The process of claim 1, wherein the 4-cyanimido-1,2-naphthoquinone is extracted from the aqueous alkaline medium with an organic solvent.

15. The process of claim 14, wherein the organic solvent is a chlorinated hydrocarbon.

16. The process of claim 15, wherein the chlorinated hydrocarbon is methylene chloride.

17. The process of claim 1 wherein the high performance liquid chromatography is carried out on a C-8 reverse phase.

18. The process of claim 17, wherein, as mobile phase for the high performance liquid chromatography, there is used a mixture of methyltrioctylammonium salt and methanol/water/buffer solution (ratio 850:100:50 to 600:350:50).

19. The process of claim 18, wherein the buffer has a pH value of 4.0 to 7.0.

20. The process of claim 19 wherein there is used 0.1 to 2.0 g. methyltrioctylammonium salt per 1000 ml. methanol/water/phosphate buffer solution.

21. The process of claim 1 wherein the 1,2-naphthoquinone-4-sulphonate is added in an at least stoichiometric amount.

* * * * *

UNITED STATES PATENT AND TRADEMARK OFFICE
CERTIFICATE OF CORRECTION

PATENT NO. : 4,692,415

DATED : September 8, 1987

INVENTOR(S) : Ulrich Rust

It is certified that error appears in the above-identified patent and that said Letters Patent is hereby corrected as shown below:

Column 3, line 10: after "sulphate" insert -- anion. Tetrabutylammonium hydrogen sulphate --.

Column 3, line 36: delete "4.0 to".

Column 3, line 40: after "water" insert -- /phosphate --.

Signed and Sealed this

Fifth Day of July, 1988

Attest:

DONALD J. QUIGG

*Attesting Officer*   *Commissioner of Patents and Trademarks*